United States Patent [19]

Marhold et al.

[11] Patent Number: 5,672,765
[45] Date of Patent: Sep. 30, 1997

[54] PROCESS FOR THE PREPARATION OF AROMATIC FLUORINATED COMPOUNDS AND NOVEL DIAMIDES

[75] Inventors: Albrecht Marhold, Leverkusen, Germany; Marianne Löhr, Selly Oak, United Kingdom; Heinrich Wamhoff, St. Augustin, Germany

[73] Assignee: Bayer Aktiengesellschaft, Leverkusen, Germany

[21] Appl. No.: 502,341

[22] Filed: Jul. 14, 1995

[30] Foreign Application Priority Data

Jul. 22, 1994 [DE] Germany ............... 44 26 133.0

[51] Int. Cl.$^6$ ............................................. C07C 45/63
[52] U.S. Cl. .................... 568/426; 568/436; 564/154; 564/152; 570/127
[58] Field of Search ................ 564/154; 568/927, 568/426, 436

[56] References Cited

U.S. PATENT DOCUMENTS 4,229,365 10/1980 Oeser et al. ........................ 260/465

FOREIGN PATENT DOCUMENTS

371563 A1 6/1990 European Pat. Off. .
371563    6/1990 European Pat. Off. .
2391990  12/1978 France .
2515146  10/1976 Germany .
1360327  11/1972 United Kingdom .

OTHER PUBLICATIONS

S. Karlsson, et al., Acta Chemica Scandinavica, B 31, pp. 399–406, (1977).

R. Ghirardelli, et al, J. Am. Chem. Soc., vol. 79, pp. 734–741 (1957).

Database Crossfire, from Reppe, et al., Justus Liebigs Ann. Chem., vol. 596, pp. 203, 212 and 1,203, (1955).

Database Crossfire, from Shepherd, et al, J. Med. Chem., vol. 5, pp. 823–855, (1962).

Database Crossfire, from Rameau, Recl. Trav. Chim. pays–Bas, vol. 57, p. 208, (1938).

Primary Examiner—Marianne M. Cintins
Assistant Examiner—Dwayne C. Jones
Attorney, Agent, or Firm—Sprung Horn Kramer & Woods

[57] ABSTRACT

Aromatic, ring-fluorinated compounds are prepared by reaction of corresponding chlorine compounds or bromine compounds with alkali metal fluorides using a diamide as solvent. Most of the diamides which can be used are novel compounds.

8 Claims, No Drawings

PROCESS FOR THE PREPARATION OF AROMATIC FLUORINATED COMPOUNDS AND NOVEL DIAMIDES

The halogen exchange reaction (=halex reaction) for the fluorination of aromatic halogen compounds is generally carried out in polar aprotic solvents such as dimethylformamide, dimethylacetamide, N-methylpyrrolidone, tetramethylene sulphone or dimethyl sulphoxide. A disadvantage of this is frequently the poor solubilities of the fluorinating agents (e.g. potassium fluoride) in the known solvents and the high reaction temperatures thus required. When halogenated nitro compounds are used, at high reaction temperatures there is a considerable risk of spontaneous decomposition. Moreover, such reactions require long reaction times.

It is therefore desirable to have solvents available for halex reactions which are able to dissolve relatively large mounts of fluorinating agents. In such solvents, the halex reaction could proceed at a lower temperature and in a shorter time, it could be carried out in a technically simpler manner and there would no longer be virtually any risk of spontaneous decomposition.

Acta Chem. Scand. B31, 399 to 406 (1977) discloses N,N'-dimethyl-N,N'-diacetylethylenediamine and N,N'-dimethyl-N,N'-diacetylpropane-1,3-diamine and physico-chemical measurements thereon.

A process has now been found for the preparation of aromatic, ring-fluorinated compounds by reaction of corresponding chlorine compounds or bromine compounds with alkali metal fluorides in a solvent, which is characterized in that the solvent used is a diamide.

For example, in the process according to the invention a diamide of the formula (I) can be used $$R^1\text{–}C(=O)\text{–}N(R^2)\text{–}B\text{–}N(R^{2'})\text{–}C(=O)\text{–}R^{1'}$$

in which

B represents a bridge of the formula (II)

$$\text{–(CH}_2\text{)}_m\text{–CH(R}^3\text{)–CH(R}^4\text{)–CH(R}^5\text{)–(X)–CH(R}^6\text{)–CH(R}^7\text{)–}_n$$

where $R^3$, $R^4$, $R^5$, $R^6$ and $R^7$, independently of each other, are each hydrogen or $C_1\text{–}C_6$-alkyl,
X=oxygen, sulphur or N—$C_1\text{–}C_6$-alkyl,
m=zero or 1 and
n=zero, 1 or 2,
$R^1$ and $R^2$, independently of each other, represent $C_1\text{–}C_6$-alkyl or together represent a bridge of the formulae —(—CH$_2$—)$_3$—, —(—CH$_2$—)$_4$—, —Y—(—CH$_2$—)$_2$—,
—Y—(—CH$_2$—)$_3$—, —(—CH$_2$—)—Y—(—CH$_2$—)—,
—(—CH$_2$—)—Y—(—CH$_2$—)$_2$— or —(—CH$_2$—)$_2$—Y—(—CH$_2$—)—, where Y=oxygen, sulphur or N—$C_{1\text{–}6}$-alkyl and
$R^{1'}$ and $R^{2'}$, independently of $R^1$ and $R^2$, have the same scope of meaning as $R^1$ and $R^2$.

In the process according to the invention, diamides of the formula (I) are preferably used in which $R^1$ and $R^2$ on the one hand and $R^{1'}$ and $R^{2'}$ on the other hand are identical.

Furthermore, in the process according to the invention, diamides are preferably used in which in formula (II) $R^4$, $R^5$, $R^6$ and $R^7$, independently of each other, each represent hydrogen or methyl. $R^4$ and $R^6$ particularly preferably represent hydrogen and $R^5$ and $R^7$ particularly preferably represent hydrogen or methyl. $R^4$, $R^5$, $R^6$ and $R^7$ are very particularly preferably each hydrogen.

Furthermore, in the process according to the invention, diamides are preferably used in which in formula (II) X represents oxygen, m zero and n zero or 1.

Furthermore, in the process according to the invention, diamides of the formula (I) are preferably used in which $R^1$, $R^2$, $R^{1'}$ and $R^{2'}$ represent methyl or ethyl or $R^1$ and $R^2$, and $R^{1'}$ and $R^{2'}$, each together denote a —(—CH$_2$—)$_3$—, —(—CH$_2$—)$_4$— or —N(CH$_3$)—(—CH$_2$—)$_2$— bridge.

Particular preference is given to use of the diamides below (Ia) $CH_3\text{–}C(=O)\text{–}N(CH_3)\text{–}CH_2\text{–}CH_2\text{–}N(CH_3)\text{–}C(=O)\text{–}CH_3$ (Ib) $CH_3\text{–}C(=O)\text{–}N(CH_3)\text{–}(CH_2)_2\text{–}O\text{–}(CH_2)_2\text{–}N(CH_3)\text{–}C(=O)\text{–}CH_3$ (Ic) pyrrolidinone-based bis-amide with —CH$_2$—CH$_2$— bridge (Id) pyrrolidinone-based bis-amide with —(CH$_2$)$_2$—O—(CH$_2$)$_2$— bridge and (Ie) N-methyl-pyrrolidinone-based bis-amide with —CH$_2$—CH$_2$— bridge The diamides to be used according to the invention can be used as individual compounds, as mixtures with each other or as mixtures with known solvents such as dimethylformamide, dimethylacetamide, N-methylpyrrolidone, tetramethylene sulphone and/or dimethyl sulphoxide. In the process according to the invention, the solvent used preferably comprises at least 5 mol % of diamides.

In the process according to the invention aromatic chlorine compounds or bromine compounds of the formula (III) can be used for example $$\text{Ar}(E^1)(E^2)(\text{Hal}_p)(\text{Cl or Br})$$

in which $E^1$ represents an electron-withdrawing substituent and
$E^2$ represents hydrogen or an electron-withdrawing substituent or
$E^1$ and $E^2$ are in the ortho position to each other and together represent —CO—N—($C_1\text{–}C_6$-alkyl)—CO—,
Hal represents fluorine, chlorine or bromine and p denotes zero or an integer from 1 to 3.

$E^1$ and $E^2$, $E^2$ if it represents an electron-withdrawing substituent, can, independently of each other, each denote, e.g., $NO_2$, CN, $CF_3$, CHO, COO—$C_1$-$C_6$-alkyl, COZ or $SO_2Z$ (where Z=fluorine, chlorine or bromine).

$E^1$ and $E^2$ are preferably in the meta position to each other and preferably in the ortho or para position to Cl or Br.

If $E^1$ and/or $E^2$ represents a COZ or $SO_2Z$ radical in which Z is not fluorine, when the process according to the invention is carried out, not only ring chlorine atoms but also Z atoms can be replaced by fluorine. Thus, for example starting from 2,4-dichlorobenzoyl chloride, 2,4-difluorobenzoyl fluoride can be prepared in the manner according to the invention.

If a plurality of ring chlorine or ring bromine atoms are present in the starting material of the formula (III), all or some of these can be replaced by fluorine. This is dependent on the position of the chlorine or bromine atoms to $E^1$ and $E^2$ and on the amount of the fluorinating agent.

In the process according to the invention, all alkali metal fluorides can be used, alone or as any mixtures with each other. Potassium fluoride is preferably used. Per equivalent of chlorine or bromine to be exchanged, 0.9 to 2 mol of alkali metal fluoride are preferably used.

The solvent to be used according to the invention can be used for example in amounts of 0.1 to 5 mol, based on 1 mol of the compound of the formula (III).

Suitable temperatures for the fluorination reaction are, for example, those in the range from 150° to 220° C. If appropriate, the fluorination reaction can be carried out in a closed vessel or under pressure, e.g. when the reaction temperature is in the vicinity of or above the boiling point of the compound of the formula (III) used or fluorination products thereof.

The fluorination can be carried out in the presence or absence of a catalyst. Possible catalysts are, for example, so-called phase transfer catalysts which can be ammonium compounds or phosphonium compounds, for example. The procedure is preferably carried out without addition of catalyst.

The reaction mixture present after the reaction according to the invention can be worked up in such a way, eg., that the ring-fluorinated aromatic compound obtained is first distilled off at atmospheric pressure or at reduced pressure. From the residue remaining, the diamide used as solvent can if appropriate be recovered by extraction or distillation and can be reused.

The diamides to be used according to the invention permit the halex reactions for the fluorination of aromatic halogen compounds to be carried out at lower temperatures, in a simpler manner, without the risk of spontaneous decomposition, with short reaction times and with good yields.

The present invention also relates to diamides of the formula (I)

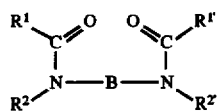

in which

B represents a bridge of the formula (II)

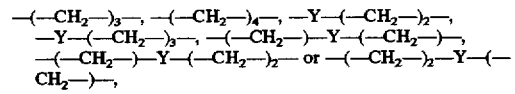

where $R^3$, $R^4$, $R^5$, $R^6$ and $R^7$, independently of each other, are each hydrogen or $C_1$-$C_6$-alkyl,
X=oxygen, sulphur or N—$C_1$-$C_6$-alkyl,
m=zero or 1 and
n=zero, 1 or 2, $R^1$ and $R^2$, independently of each other, represent $C_1$-$C_6$-alkyl or together represent a bridge of the formulae —(—$CH_2$—)$_3$—, —(—$CH_2$—)$_4$—, —Y—(—$CH_2$—)$_2$—,
—Y—(—$CH_2$—)$_3$—, —(—$CH_2$—)$_2$—Y—(—$CH_2$—)$_2$—,
—(—$CH_2$—)$_2$—Y—(—$CH_2$—)$_2$— or —(—$CH_2$—)$_2$—Y—(—$CH_2$—)—, where Y=oxygen, sulphur or N—$C_{1-C_6}$-alkyl and
$R^{1'}$ and $R^{2'}$, independently of $R^1$ and $R^2$, have the same scope of meaning as $R^1$ and $R^2$, except the compounds in which B represents $(CH_2)_2$ or $(CH_2)_3$ and $R^1$, $R^2$, $R^{1'}$ and $R^{2'}$ are each methyl.

Preferred diamides according to the invention are those of the formula (I) in which B represents a bridge of the formula (II) in which $R^4$, $R^5$, $R^6$ and $R^7$, independently of each other, represent hydrogen or methyl, X represents oxygen, m represents zero and n represents zero or 1 and $R^1$, $R^2$, $R^{1'}$ and $R^{2'}$ are identical and each represent methyl or ethyl or $R^1$ and $R^{1'}$, and $R^2$ and $R^{2'}$, each together represent a —(—$CH_2$—)$_3$—, —(—$CH_2$—)$_4$— or —N($CH_3$)—(—$CH_2$—)$_2$— bridge, except the compounds in which B represents $(CH_2)_2$ or $(CH_2)_3$ and $R^1$, $R^2$, $R^{1'}$ and $R^{2'}$ each represent methyl.

Particularly preferred diamides according to the invention correspond to the formulae (Ib), (Ic), (Id) and (Ie).

Diamides according to the invention and which can be used in the fluorination process according to the invention can be prepared, e.g., by reacting 1 mol of a compound of the formula Cl—B—Cl in which B has the meaning given under formula (II) with 2 mol of an amine of the formula $R^1$—CO—NH—$R^2$ in which $R^1$ and $R^2$ have the meaning given under formula (I). This procedure can be carried out with addition of bases, in the presence of solvents and with the ejection of the resulting water.

1 mol of a compound of the formula $R^2$—NH—B—NH—$R^2$ in which $R^2$ represents $C_1$-$C_6$-alkyl and B has the meaning given under formula (II) can also be reacted with 2 mol of a compound of the formula $C_1$-$C_6$-alkyl-CO—Cl. This process is suitable for the preparation of diamides of the formula (I) in which $R^1$, $R^2$, $R^{1'}$ and $R^{2'}$ represent $C_1$-$C_6$-alkyl.

Diamides of the formula (I) in which $R^1$ and $R^2$, and $R^{1'}$ and $R^{2'}$, each form a bridge of the formulae specified above can be prepared by first reacting 1 mol of a compound of the formula $H_2N$—B—$NH_2$ in which B has the meaning specified under formula (II) with 2 mol of a compound of the formula Cl—Q—COCl in which Q denotes a bridge of the formula which $R^1$ and $R^2$ can form together, an intermediate compound of the formula

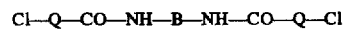

being formed and this intermediate compound being converted by strong alkali into a compound of the formula (I) in which $R^1$ and $R^2$, and $R^{1'}$ and $R^{2'}$, form a bridge of the formulae specified above.

Furthermore, 1 mol of a compound of the formula

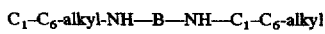

can also be reacted with an excess of an anhydride of the formula

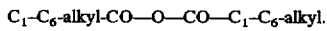

Compounds of the formula (I) may be prepared in this way, in which $R^1$, $R^2$, $R^{1'}$ and $R^{2'}$ represent $C_1$–$C_6$-alkyl.

EXAMPLES

EXAMPLE 1

Preparation of the compound of the formula (Ia)

106.5 ml of 1,2-bis-(methylamino)-ethane were introduced under ice cooling and then 377.5 ml of acetic anhydride were added dropwise over the course of 2 hours. The mixture was then stirred at room temperature for a further 4 hours. The reaction mixture obtained was worked up by fractional distillation in vacuo. At 125° to 130° C./0.75 mbar, the compound of the formula (Ia) was separated off and then recrystallized from benzine (boiling range 80° to 110° C.). 193.0 g (=89.3% of theory) of product were obtained having a melting point of 92.5° C.

EXAMPLE 2

Preparation of the compound of the formula (Id)

106.5 ml of 2-pyrrolidinone were introduced into 730 ml of dimethyl sulphoxide and 94.1 g of powdered potassium hydroxide and 3.0 g of N-benzyl-4-N,N'-dimethylaminopyridinium chloride (catalyst) were added. 82.0 ml of bis(2-chloroethyl) ether were added dropwise under ice cooling in the course of 45 minutes and the mixture was stirred for a further 60 hours at room temperature. The potassium chloride formed was first filtered off from the reaction mixture obtained and washed with 300 ml of tetrahydrofuran. The filtrate and the wash liquid were combined, the solvent was separated off in vacuo, potassium chloride again precipitating was filtered off and the crude product was fractionally distilled. At 168° to 170° C./0.5 mbar, 143.0 g (=85.47% of theory) of the compound of the formula (Id) were obtained in the form of a yellow oil. The product had a refractive index $n_D^{20}$=1.5089 and the $^1$H-NMR spectrum (200 MHz DMSO) had characteristic bands at δ=1.95, 2.24, 3.36, 3.41 and 3.53 ppm, and the IR spectrum had characteristic bands at 2900, 1680, 1493, 1460, 1300 and 1134 cm$^{-1}$.

EXAMPLE 3

Preparation of the compound of the formula (Ib)

110.0 g of N-methylacetamide, 101.0 g of potassium hydroxide and 750 ml of dimethyl sulphoxide were mixed at room temperature and stirred for 45 minutes. After addition of 3.0 g of N-benzyl-4-N,N'-dimethylaminopyridinium chloride (catalyst) and cooling of the mixture to 10° C., 88.0 ml of bis-(2-chloroethyl) ether were added dropwise in the course of 55 minutes and the mixture was then stirred for a further 40 hours at room temperature. The reaction mixture was worked up as described in Example 2. In the distillation, three fractions containing the compound of the formula (Ib) arose: a) 133° to 138° C./0.5 mbar, 81.9% pure—21.0 g, b) 138° to 142° C./0.5 mbar, 100% pure—11.0 g and c) 142° to 144° C./0.5 mbar, 98.0% pure—4.0 g.

The following parameters were measured on fraction b): refractive index $n_D^{20}$=1.4842, $^1$H-NMR spectrum (200 MHz, CDCl$_3$) having characteristic bands at δ=2.09, 2.11, 2.12, 2.94, 3.04, 3.07 and 3.54 ppm and IR spectrum having characteristic bands at 2900, 1480, 1440 to 1410, 1360, 1125 and 1030 cm$^{-1}$.

EXAMPLE 4

Preparation of the compound of the formula (Ic)

a) 1st stage

A mixture of 20.0 ml of 1,2-diaminoethane and 200 ml of toluene was introduced under ice cooling and 56.0 ml of 4-chlorobutyric chloride, dissolved in 400 ml of toluene, were added dropwise thereto in the course of 2 hours. The hydrogen chloride released was bound by addition of 23.75 g of pyridine. After stirring for 2 hours at room temperature, the reaction mixture was filtered off by suction, washed with 600 ml of water and the filter cake was dried at 70° C. In this manner, 75.0 g (=93.0% of theory) of N,N'-di-4-chloro-1-oxobutyl-1,2-diaminoethane were obtained in the form of a white solid having the melting point 138° to 139.5° C.

b) 2nd stage 135.3 g of potassium hydroxide were heated to 60° C. in 4.0 l of toluene. After the addition of 3.0 g of N-benzyl-4-N,N'-dimethylaminopyridinium chloride (catalyst) and 243.0 g of the product obtained in the 1st stage, the internal temperature increased to 98° to 100° C., the solid obtained in the 1st stage dissolving with yellow coloration. At this temperature the mixture was stirred for a further 1 hour under reflux. The mixture was then cooled and solid constituents (essentially potassium chloride) were filtered off. The solvent was removed from the titrated in vacuo, a crude product having a purity of 97.2% precipitating out in the form of pale yellow needles. These were filtered off and recrystallized from cyclohexane. 84.0 g (47.2% of theory) of the compound of the formula (Ic) were thus obtained in the form of colourless needles having a melting point of 106° to 108° C. The $^1$H-NMR spectrum (200 MHz, CDCl$_3$) showed characteristic bands at δ=1.99, 2.32. 3.45 and 3.48 ppm, and the IR spectrum showed characteristic bands at 2930, 1670, 1467, 1430 and 1298 cm$^{-1}$.

EXAMPLE 5

Fluorination using the compound of the formula (Ia)

36.3 g of potassium fluoride were added to 113.0 g of the compound of the formula (Ia) and traces of water were removed from this mixture by initial distillation. 96.0 g of 3,4-dichloronitrobenzene were then added and the mixture was stirred at 190° C. for 5.75 hours. From the reaction mixture, steam distillation then gave 82.0 g of an organic phase which comprised 97.5% of 3-chloro-4-fluoro-nitrobenzene. This corresponds to a yield of 91.2% of theory.

Comparison

Example 5 was repeated, but the solvent used was an equivalent amount of tetramethylene sulphone. After a reaction time of 22 hours, 3-chloro-4-fluoro-nitrobenzene was obtained in a yield of 32.8% of theory.

EXAMPLE 6

Fluorination using the compound of the formula (Ic)

27.4 g of potassium fluoride were added to 97.0 g of the compound of the formula (Ic) and traces of water were removed from this mixture by initial distillation. 72.5 g of 3,4-dichloronitrobenzene were then added and the mixture was stirred for 6 hours at 190° C. Salts present in the reaction mixture were removed therefrom by filtration and washed with 400 ml of methylene chloride. The titrated and the wash liquid were combined, concentrated in vacuo and, after addition of 300 ml of water, subjected to steam distillation. 46.4 g of 3-chloro-4-fluoro-nitrobenzene were obtained. This corresponds to a yield of 70.0% of theory.

EXAMPLE 7

Fluorination using the compound of the formula (Id)

25.2 g of potassium fluoride were added to 113.0 g of the compound of the formula (Id) and traces of water were removed from this mixture by initial distillation. 69.2 g of 3,4-dichloronitrobenzene were then added and the mixture was stirred at 190° C. for 4.5 hours. The reaction mixture was worked up as specified in Example 6. 30.3 g of 3-chloro-4-fluoro-nitrobenzene were obtained. This corresponds to a yield of 48.1% of theory.

EXAMPLE 8

Fluorination using a mixture of the compound of the formula (Ib) with tetramethylene sulphone 24.0 g of sulfolane and 18.6 g of potassium fluoride were added to 20.0 g of the compound of the formula (Ib) and traces of water removed from this mixture by initial distillation. 51.9 g of 3,4-dichloronitrobenzene were then added and the batch was stirred at 190° C. for 12.75 hours. The reaction mixture was worked up as specified in Example 5. 29.84 g of 3-chloro-4-fluoro-nitrobenzene were obtained. This corresponds to a yield of 63.5% of theory.

EXAMPLE 9

Fluorination using a mixture of the compound of the formula (Ia) with tetramethylene sulphone 278 g of potassium fluoride were suspended in 600 ml of tetramethylene sulphone and 42 g of the compound (Ia) and were initially distilled at 15 mbar. 299 g of N-methyltetrachlorophthalimide were then added and the mixture was stirred at 165° C. for 5 hours with the exclusion of moisture. It was then determined by GC analysis that more than 98% of the starting material had been fluorinated to give N-methyl-tetrafluorophthalimide. The reaction mixture was stirred into 2 l of water, the sediment precipitating out was filtered off by suction, washed with water and dried. The yield was 215 g=92% of theory (melting point: 132° C.).

EXAMPLE 10 (for comparison)

The procedure was followed as in Example 9, but no compound of the formula (Ia) was used. GC analysis after 5 hours at 165° C. indicated that in total 18% by weight of incompletely fluorinated compounds were present in the reaction mixture. After stirring for a further 3 hours at 190° C., all of the starting material and all of the incompletely fluorinated compounds had reacted to completion to give N-methyltetrafluorophthalimide.

EXAMPLE 11

Fluorination using a mixture of the compound of the formula (Ia) with tetramethylene sulphone To a suspension of 240 g of potassium fluoride in 380 ml of tetramethylene sulphone were added 60 g of the compound (Ia) and 50 ml of xylene. Traces of water were removed from this mixture by distilling off together with the xylene. 284 g of 2-H-tetrachlorobenzotrifluoride were then added and the mixture was stirred at 190° C. for 8 hours with exclusion of moisture. The volatile constituents of the reaction mixture were then distilled off under reduced pressure and the distillate was subjected to a fine distillation at atmospheric pressure. 108 g of 5-chloro-2,3,4-trifluorobenzotrifluoride were obtained having a boiling point of 134°–135° C. and a refractive index of $n_D^{20}$= 1.4120.

EXAMPLE 12 (for comparison)

The procedure was followed as in Example 11, but no compound of the formula (Ia) was used. The yield of 5-chloro-2,3,4-trifluorobenzotrifluoride was 67 g.

What is claimed is:

1. A process for the preparation of aromatic, ring-fluorinated compounds by reaction of corresponding chlorine compounds or bromine compounds with alkali metal fluorides in a solvent, comprising using a diamide as a solvent.

2. The process of claim 1, in which the diamide is of the formula (I)

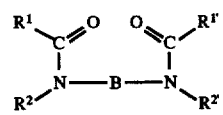

in which

B represents a bridge of the formula (II)

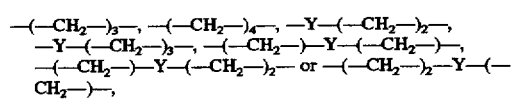

where $R^3$, $R^4$, $R^5$, $R^6$ and $R^7$, independently of each other, are each hydrogen or $C_1$-$C_6$-alkyl,
X=oxygen, sulphur or N—$C_1$-$C_6$-alkyl,
m=zero or 1 and
n=zero, 1 or 2,
$R^1$ and $R^2$, independently of each other, represent $C_1$-$C_6$-alkyl or together represent a bridge of the formulae —(—CH$_2$—)$_3$—, —(—CH$_2$—)$_4$—, —Y—(—CH$_2$—)$_2$—,
—Y—(—CH$_2$—)$_3$—, —(—CH$_2$—)—Y—(—CH$_2$—)—,
—(—CH$_2$—)—Y—(—CH$_2$—)$_2$— or —(—CH$_2$—)$_2$—Y—(—CH$_2$—)—, where Y=oxygen, sulphur or N—$C_1$-$C_6$-alkyl and
$R^{1'}$ and $R^{2'}$, independently of $R^1$ and $R^2$, have the same scope of meaning as $R^1$ and $R^2$.

3. The process of claim 2, in which a diamide is used in which in formula (II) $R^4$, $R^5$, $R^6$ and $R^7$, independently of each other, each represents hydrogen or methyl, X represents oxygen, m represents zero and n represents zero or 1 and in formula (I) $R^1$, $R^2$, $R^{1'}$ and $R^{2'}$ represent methyl or ethyl or $R^1$ and $R^2$, and $R^{1'}$ or $R^{2'}$, each together denote a

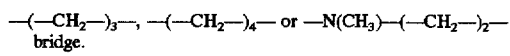
bridge.

4. The process of claim 1, in which a diamide of the formulae (Ia) to (Ie) is used

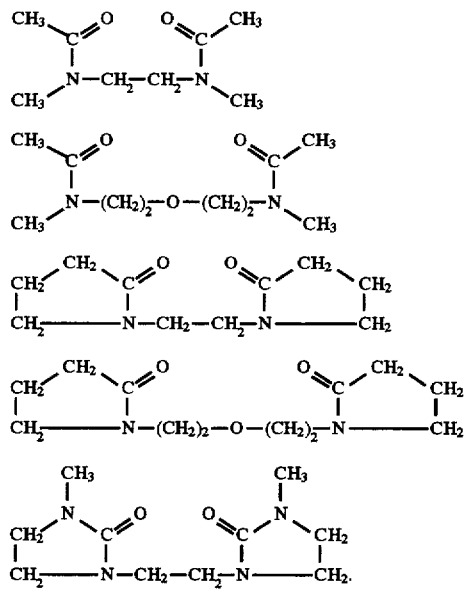

5. The process of claim 1, in which aromatic chlorine compounds or bromine compounds of the formula (III) are used

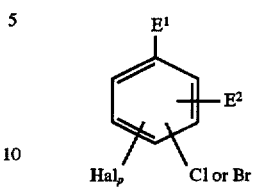

in which $E^1$ represents an electron-withdrawing substituent and $E^2$ represents hydrogen or an electron-withdrawing substituent or $E^1$ and $E^2$ are in the ortho position to each other and together represent —CO—N—($C_1$-$C_6$-alkyl)—CO—, Hal represents fluorine, chlorine or bromine and p denotes zero or an integer from 1 to 3.

6. The process of claim 5, in which in formula (III) $E^1$ and $E^2$, $E^2$ if it represents an electron-withdrawing substituent, independently of each other, each denote $NO_2$, CN, $CF_3$, CHO, COO—$C_1$-$C_6$-alkyl, COZ or $SO_2Z$, where Z=fluorine, chlorine or bromine.

7. The process of claim 1, in which per equivalent of chlorine or bromine to be exchanged, 0.9 to 2 mol of alkali metal fluoride are used.

8. The process of claim 1, which is carried out at 150° to 220° C.

* * * * *